United States Patent [19]

Campos Pino

[11] Patent Number: 4,961,933

[45] Date of Patent: Oct. 9, 1990

[54] PREPARATION FOR RELIEF OF MUSCLE AND JOINT ACHES

[76] Inventor: Longino S. Campos Pino, 103 Thayer St., New York, N.Y. 10040

[21] Appl. No.: 132,219

[22] Filed: Dec. 14, 1987

[51] Int. Cl.$^5$ .................. A61K 33/34; A61K 35/78
[52] U.S. Cl. .................. 424/630; 424/195.1; 424/635; 514/825; 514/906
[58] Field of Search .................. 424/140, 141, 195.1, 424/630, 635; 514/825, 906

[56] References Cited

U.S. PATENT DOCUMENTS

| | | | |
|---|---|---|---|
| 55,234 | 6/1866 | Bode | 424/147 |
| 92,065 | 6/1869 | Lighthall | 424/195.1 X |
| 923,999 | 6/1909 | Riggs | 424/127 X |
| 1,620,490 | 3/1927 | Sanders | 424/143 |
| 4,271,154 | 6/1981 | Richards | 424/195.1 |
| 4,680,309 | 7/1987 | Maurer | 514/499 |

FOREIGN PATENT DOCUMENTS 3909 of 1910 United Kingdom ............. 424/195.1

OTHER PUBLICATIONS

Lust, *The Herb Book*, First Edition, pp. 147–148 (1974).
Kloss, *Back to Eden*, pp. 215–230 (1939).

*Primary Examiner*—John W. Rollins
*Assistant Examiner*—W. Catchpole
*Attorney, Agent, or Firm*—Natter & Natter

[57] ABSTRACT

The invention features a medicament for simple relief of aches and pains. An aqueous solution of cayenne, alcohol and copper oxide in solution is applied to affected, aching joints and muscles by topical application. After drying, the solution imparts a soothing warmth and heating to the pained areas.

5 Claims, No Drawings

PREPARATION FOR RELIEF OF MUSCLE AND JOINT ACHES

Field of the Invention

The invention relates to medicaments useful for the, treatment of pain and discomfort in muscles and joints in a mammalian host, and especially to a remedy which utilizes the therapeutic properties of medicinal herbs in combination with other ingredients.

In particular, the preparation of this invention includes cuprum and cayenne, derived from capsicum, as constitutent components.

Background of the Invention

There are numerous remedies that are sold over-the-counter for the relief of minor arthritic and rheumatic pain. Many of these products feature oil substances which not only stain adjacent clothing, but further do not readily penetrate the effected areas.

The invention pertains to a penetrating aqueous medicament which is applied to the surface of the skin, dries quickly and leaves no residue to foul and stain clothing. The aqueous solution of the invention has as one of its objectives to use readily available ingredients, whereby the user of the medicament can prepare the solution, if he so chooses. Another object of the invention is to utilize the natural properties of cayenne.

The aqueous preparation has as its main ingredients: copper oxide in solution as achieved by the addition of 30 c.c. of copper filings to 280 c.c. of water and 140 c.c. of blended cayenne; added to 140 c.c. of a 70% solution of isopropyl alcohol.

As is readily obvious from the above recitation of components, the solution is comprised of easily obtainable ingredients suitable for household preparation.

The solution of the invention is externally daubed upon the skin of effected and painful joints or muscles, and allowed to dry. Drying takes place very rapidly; usually within a few minutes. After application the solution is allowed to remain for at least 12 hours upon the painful area. Usually within 30 minutes after application, a warmth is experienced in the effected area that appears to bring relief from the pain.

A continuing relief is provided by an application of the solution either once or twice daily over a period of 3 to 5 days.

While copper oxides (either the cuprous or cupric oxide) are not readily soluble in water, the addition of the cayenne to the water assists the copper oxides into solution by providing an acidic environment. The copper oxides are formed by boiling the solution of cayenne and water containing the copper filings.

Discussion of Related Art

The use of pure copper, as in bracelets to be worn by the individual, has been used as a means of furnishing relief for arthritic pain. The effectiveness of such use, however, has long been in controversy.

It is also known that copper salts and copper which is not in its elemental form has medicinal effects. In U.S. Pat. No. 923,999, issued June 8, 1909, copper sulfate is used in a preparation for hair tonic useful for the treatment of Eczema and dandruff.

The hydroxide, sulfate and carbonate forms of copper have also been known for their fungicidal properties. Such a teaching is to be found in the patent to: G. E. Sanders, U.S. Pat. No. 1,620,490, issued March 8, 1927.

Dry pulverized copper has also been used for rheumatism in the wearing of pads containing the copper and other ingredients. However, such benefit is claimed to be derived from an electric effect upon the body. Such a teaching can be found in U.S. Pat. No. 92,065, issued June 29, 1869, and in U. S. Pat. No. 55,234, issued June 5, 1866.

Brief Summary of the Invention

The invention is for a medicinal preparation or medicament that can be prepared at home for the simple relief of minor aches and pains caused by arthritis, neuralgia, rheumatism, etc. is a mammalian host. A small quantity of copper filings is boiled at a temperature of approximately 100° C., in a solution of blended cayenne and water for approximately three minutes. A 70% solution of isopropyl alcohol is added to the mixture which is then agitated or shaken periodically over a duration of a few days. After periodically shaking the admixture, it is filtered to remove substantially all of the copper solids.

The resulting solution is then externally applied to the surface of the skin surrounding a painful joint or muscle. The solution is allowed to dry and is maintained at the affected area for at least 12 hours. Application of the solution can be continued over a 3 to 5 day period applying the solution once or twice daily.

While it is not fully understood from where the aforementioned preparation obtains its efficacy, it is believed that the cayenne contains an active irritant for supplying heat to the tissues, and also furnishes an acid environment for allowing the dissolution of some of the copper oxides into the water. It is also believed that the cayenne when dissolved in alcohol, releases capsaicin, a substance having analgesic properties.

Detailed Description of the Invention

Generally speaking, the invention relates to simple relief of aches and pains by a solution prepared by the following example.

EXAMPLE

Blend 80 grams of cayenne and 280 grams of tap water in a blender at moderate speed until a puree is formed.

To this puree is added 18 grams of copper filings (U.S.P.) using a steel pot. The resulting admixture is then boiled for three minutes over a low flame. The boiled admixture is then decanted into a glass beaker and allowed to cool to ambient temperature.

The admixture is shaken for approximately one minute every eight hours over a forty-eight hour span. Then 125 grams of a 70% solution of isopropyl alcohol is added. The admixture is then shaken every eight hours over a period of twenty-four hours for approximately one minute each time.

The admixture is then filtered using a fine steel mesh of appropriate grade for removing the copper filings from the solution.

The solution of the example can be administered by applying it with a sterile gauze pad to effected areas such as aching joints and muscles. The solution should be shaken for a few seconds before each use.

The resulting solution has been found to have a useful shelf life of approximately eight months.

Although filings of zinc, silver and gold had been separately substituted in place of the copper, the resulting products were not found as effective in their pain relieving properties.

With these ends in view, the preparation of this invention finds embodiment in certain combinations of ingredients by which the aforementioned objects and certain other objects are hereinafter attained, and the scope of which is more particularly pointed out in the appended claims.

Having thus described the invention, there is claimed as new and desired to be secured by Letters Patent:

1. A method of preparing an aqueous solution for treating aching muscles and joints of a mammalian host by external application of said aqueous solution thereto, said method comprising the steps of:
    (a) blending approximately 80 grams of capsicum in approximately 280 grams of water to form a puree;
    (b) adding to said puree approximately 18 grams of copper filings (U.S.P.) to form a first admixture;
    (c) boiling said first admixture for approximately three minutes;
    (d) allowing said first admixture to cool to ambient temperature;
    (e) shaking said first admixture over a period of approximately forty-eight hours;
    (f) adding about 125 grams of 70% solution of isopropyl alcohol to said first admixture forming a second admixture thereby;
    (g) shaking said second admixture over a period of approximately twenty-four hours; and
    (h) filtering said second admixture to remove substantially all of said copper solids to provide said aqueous solution.

2. A method of using the solution prepared in accordance with the process of claim 1 for treating aching muscles and joints of a mammalian host including the steps of:
    daubing said solution upon the aching areas of said mammalian host in an amount sufficient to cover said aching areas, and
    allowing the solution to dry.

3. A method of using said solution as claimed in claim 2 further including the step of shaking the solution for a few seconds before daubing the solution upon the aching areas.

4. A method of using said solution as claimed in claim 2 further including the step of allowing the dried solution to remain upon the aching areas for at least twelve hours after application thereof.

5. A method of using said solution as claimed in claim 4 further including the step of daubing the solution upon the aching areas once or twice daily over a period of 3 to 5 days.

* * * * *